United States Patent
Al Ahmad et al.

(10) Patent No.: US 11,327,015 B2
(45) Date of Patent: May 10, 2022

(54) SYSTEM AND PARAMETRIC METHOD FOR CANCER DISCRIMINATIONS

(71) Applicant: United Arab Emirates University, Al Ain (AE)

(72) Inventors: Mahmoud Al Ahmad, Al Ain (AE); Ayshathul Fouzia Abdulgani, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 17/203,015

(22) Filed: Mar. 16, 2021

(65) Prior Publication Data

US 2022/0018770 A1    Jan. 20, 2022

Related U.S. Application Data

(62) Division of application No. 16/928,620, filed on Jul. 14, 2020, now Pat. No. 10,989,658.

(51) Int. Cl.
*G01N 21/59* (2006.01)
*G01N 33/483* (2006.01)

(52) U.S. Cl.
CPC ......... *G01N 21/59* (2013.01); *G01N 33/4833* (2013.01)

(58) Field of Classification Search
None
See application file for complete search history.

(56) References Cited

PUBLICATIONS

Matthew J. Hayat, "Cancer Statistics, Trends, and Multiple Primary Cancer Analyses from the Surveillance, Epidemiology, and End Results (SEER) Program", Article, 2007, 20-37, vol. 12, No. 1, The Oncologist.
V.T. Broadbridge, "Do Metastatic Colorectal Cancer Patients Who Present with Late Relapse after Curative Surgery Have a Better Survival?", Journal, 2013, 1338-1343, vol. 109, British Journal of Cancer.
Sabyasachi Mukhopadhyay, "Optical Diagnosis of Cervical Cancer by Intrinsic Mode Functions", Paper, 2017, 1-6, vol. 10063, Dynamics and Fluctuations in Biomedical Photonics XIV.
Yangbo Chen, "A Technique to Improve the Empirical Mode Decomposition in the Hilbert-Huang Transform", Article, Jun. 2003, 75-85, vol. 2, No. 1, Earthquake Engineering and Engineering Vibration.
Shao-Yin Li, "Detection of Nasopharyngeal Cancer Using Confocal Raman Spectroscopy and Genetic Algorithm Technique", Journal, Dec. 2012, 1-7, vol. 17, No. 12, Journal of Biomedical Optics.
Shiyamala Duraipandian, "In Vivo Diagnosis of Cervical Precancer Using Raman Spectroscopy and Genetic Algorithm Techniques", Paper, 2011, 4328-4336, vol. 136, Analyst—The Royal Society of Chemistry.
Maria Angela Franceschini. "Frequency-Domain Techniques Enhance Optical Mammography Initial Clinical Results", Journal, Jun. 1997, 6468-6473, vol. 94, Medical Sciences—Proceedings of the National Academy of Sciences of the United States of America.
Elena Salomatina, "Optical Properties of Normal and Cancerous Human Skin in the Visible and Near-Infrared Spectral Range", Dec. 2006, 1-9, vol. 11, No. 6, Journal of Biomedical Optics.
Par R. Prony, "Experimental Test and Analytics—On the Laws of the Dilatability of Elastic Fluids and on those of the Expansive Force of Water Vapor and Alcohol Vapor, at Different Temperatures", Journal, Dec. 2003, 24-35.
J.F. Hauer, "Application of Prony Analysis to the Determination of Modal Content and Equivalent Models for Measure Power System Response", Journal, Aug. 1991, 1062-1068, vol. 6, No. 3, Transactions on Power Systems.
C.W. Chuang, "Natural Resonances of Radar Targets via Prony's Method and Target Discriminations", Journal, Sep. 1976, 583-589, vol. 12, No. 5, IEEE Transactions on Aerospace and Electronic Systems.
Y. Huo, "Breast Tumor Characterization via Complex Natural Resonances", Article, 2003, 387-390, IEEE MTT-S Digest.
Liang Wang, "Ultra-Wide Bandwidth Based Tumor Poles Extraction in Practical Noise Situation", Article, 2016, 1-3, IEEE.
Marwa H. Bannis, "Breast Cancer Detection and Identification using Prony's Method", Article, 2014, 1926-1927, IEEE AP-S 2014.
P.K. Gale, "Prony Analysis Based Parameter Estimation of an NMR Signal of Blood Plasma for Cancer Detection", Article, 1995, 1185-1188, IEEE.
M. Roy, "Novel Approach to Power Spectrum Estimation of DNA Sequence by Prony's Method", Article, 2012, 314-317, 2012 International Conference on Communications, Devices and Intelligent Systems (CODIS).
Mahmoud Al Ahmad, "Label-Free Cancer Cells Detection Using Optical Sensors", Journal, 2017, 1-8, IEEE Access.
Daniel Potts, "Parameter Estimation for Exponential Sums by Approximate Prony Method", Journal, 2010, 1631-1642, vol. 90, Signal Processing.
Yan Jun, "Prony Algorithm's Application on Extracting the Parameters of the Power System Transient Fault", Journal, 2014, 3877-3880, vols. 602-605, Applied Mechanics and Materials—Trans Tech Publications.
Weiwei Dai, "A Nonlinear Generalization of the Savitzky-Golay Filter and the Quantitative Analysis of Saccades", Journal, 2017, 1-15, vol. 17, No. 9, Journal of Vision.
A. Fernandez Rodriguez, "Coding Prony's Method in MATLAB and Applying it to Biomedical Signal Filtering", Article, 2018, 1-14, vol. 19, BMC Bioinformatics.

(Continued)

*Primary Examiner* — Robert J Yamasaki
(74) *Attorney, Agent, or Firm* — Hayes Soloway PC

(57) ABSTRACT

There is provided a system and method for detection of cancerous cells from an organ tissue. The system includes a plurality of cells obtained from the organ tissue, a light source for directing light through the plurality of cells and an image sensor for detecting and measuring optical transmission characteristics of the plurality of cells. The proposed method includes modeling the measured optical transmission characteristics using a statistical algorithm and calculating a figure of merit (FOM) for each of the plurality of cells for enhancing identification accuracy of cancerous cells, wherein the FOM is calculated from pole coefficients and locations corresponding to the plurality of cells.

7 Claims, 10 Drawing Sheets

(56) References Cited

PUBLICATIONS

Andrew I. Su, "Molecular Classification of Human Carcinomas by Use of Gene Expression Signatures", Journal, Oct. 15, 2001, 7388-7393, vol. 61, Cancer Research.

Sridhar Ramaswamy, "Multiclass Cancer Diagnosis Using Tumor Gene Expression Signatures", Journal, Dec. 18, 2001, 15149-15154, vol. 98, No. 26, PNAS—Medical Sciences.

Zhi-Hua Zhou, "Lung Cancer Cell Identification Based on Artificial Neural Network Ensembles", 2002, 25-36, vol. 24, Artificial Intelligence in Medicine.

Kamesh Munagala, "Cancer Characterization and Feature Set Extraction by Discriminative Margin Clustering", Article, 2004, vol. 5, BMC Bioinformatics.

Stephanie Ma, "Indentification and Characterization of Tumorigenic Liver Cancer Stem/Progenitor Cells", Journal, 2007, 2542-2556, vol. 132, Gastroenterology.

Song-Bin Huang, "Classification of Cells with Membrane Staining and/or Fixation Based on Cellular Specific Membrane Capacitance and Cytoplasm Conductivity", Article, 2015, 163-171, vol. 6, Micromachines.

Kang Zhao, "Single-Cell Electrical Phenotyping Enabling the Classification of Mouse Tumor Samples", Article, 2016, 1-8, Nature—Scientific Reports.

Mahmoud Al Ahmad, "Electrical Characterization of Normal and Cancer Cells", Article, Feb. 2017, 1-9, IEEE Access.

G.L. Wright Jr., "Proteinchip Surface Enhanced Laser Desorption/Ionization (SELDI) Mass Spectrometry: A Novel Protein Biochip Technology for Detection of Prostate Cancer Biomarkers in Complex Protein Mixtures", Journal, 1999, 264-276, vol. 2, Prostate Cancer and Prostatic Diseases—Macmillan Publishers.

S. Kumar, "Biomarkers in Cancer Screening, Research and Detection: Present and Future: a Review", Journal, 2006, 385-405, vol. 11, No. 5, Biomarkers—Informa Healthcare.

Wenwei Xu, "Cell Stiffness is a Biomarker of the Metastatic Potential of Ovarian Cancer Cells", Journal, Oct. 2012, 1-12, vol. 7, No. 10, PLOS One.

Yi Jun Yang, Md, Phd, "Comparison of Needle Core Biopsy and Fine-Needle Aspiration for Diagnostic Accuracy in Musculoskeletal Lesions", Journal, Jul. 2004, 759-764, vol. 128, Archives of Pathology & Laboratory Medicine.

Gengfeng Zheng, "Multiplexed Electrical Detection of Cancer Markers with Nanowire Sensor Arrays", Article, Oct. 2005, 1294-1301, vol. 23, No. 10, Nature Biotechnology.

Lisa A. Flanagan, "Unique Dielectric Properties Distinguish Stem Cells and Their Differentiated Progeny", Journal, 2008, 656-665, Dielectric Properties of Neural Stem Cells—Stem Cells.

Guogeng Qiao, "Bioimpedance Analysis for the Characterization of Breast Cancer Cells in Suspension", Journal, Aug. 2012, 2321-2329, col. 59, No. 8, IEE Transactions on Biomedical Engineering.

Malgorzata Lekka, "Discrimination Between Normal and Cancerous Cells Using AFM", Article, 2016, 1-16, BioNanSci, Springer.

Naoko Fujioka, "Differences Between Infrared Spectra of Normal and Neoplastic Human Gastric Cells", Journal, 2004, 59-66, vol. 18, Spectroscopy.

Xiaohua Huang, "Gold Nanoparticles: Interesting Optical Properties and Recent Applications in Cancer Diagnostics and Therapy", Journal, 2007, 681-693, vol. 2, No. 5, Nanomedicine—Future Medicine.

Jinjin Yin, "Label-Free and Turn-On Aptamer Strategy for Cancer Cells Detection Based on a DNA-Silver Nanocluster Fluorescence Upon Recognition-Induced Hybridization", Article, 2013, 1-9, Analytical Chemistry—American Chemical Society.

Ammara Masood, "Self-Supervised Learning Model for Skin Cancer Diagnosis", Article, Apr. 2015, 1012-1015, 7th Annual International IEEE EMBS Conference on Neural Engineering.

A. Abdulsadda, "Stability Analysis and Breast Tumor Classification from 2D ARMA Models of Ultrasound Images", Article, Sep. 2009, 3763-3766, 31st Annual International Conference of the IEEE EMBS.

Ana Rita Lima, "Discrimination Between the Human Prostate Normal and Cancer Cell Exometabolome by GC-MS", Journal, 2018, 1-12, vol. 8, Nature—Scientific Reports.

Fabian Eduardo Giana, "Assay Based on Electrical Impedance Spectroscopy to Discriminate Between Normal and Cancerous Mammalian Cells", Journal, 2018, 1-10, vol. 97, No. 3, Physical Review—American Physical Society.

Taejin Ahn, "Deep Learning-Based Identification of Cancer of Normal Tissue Using Gene Expression Data", Article, 2018, 1748-1752, 2018 IEEE International Conference on Bioinformatics and Biomedicine (BIBM).

Mutsumi Takagi, "Noninvasive Discrimination Between Human Normal and Cancer Cells by Analysis of Intracellular Distribution of Phase-Shift Data", Article, 2015, 1-7, Cytotechnology—Springer.

Hirotugu Akaike, "Fitting Autoregressive Models for Prediction", Article, Jun. 17, 1969, 243-247, The Institute of Statistical Mathematics.

Jeffrey Ayres, "Analog Circuit Testing Using Auto Regressive Moving Average Models", Article, 2007, 1-6, 20th International Conference on VLSI Design—IEEE Computer Society.

T.W. Anderson, "Estimation for Autoregressive Moving Average Models in the Time and Frequency Domains", Journal, Sep. 1977, 842-865, vol. 5, No. 5, The Annals of Statistics—The Institute of Mathematical Statistics.

Nida, Nasir and Mahmoud Al Ahmad, "Measuring Transmittance of Human Female Breast Cells through Spectrophotometry and Generating its Equivalent Circuit by Prony Modelling", Article, 2017, 1-5, 4th IEEE International Conference on Engineering Technologies and Applied Sciences (ICETAS), IEEE.

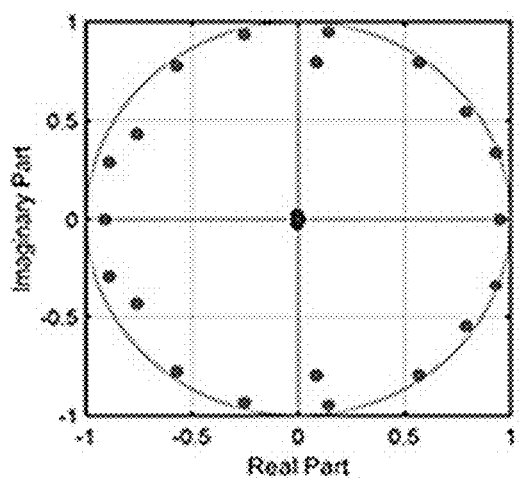 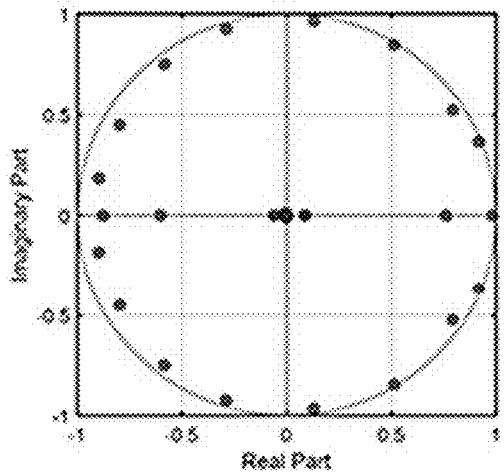
Fig. 3A  Fig. 3B
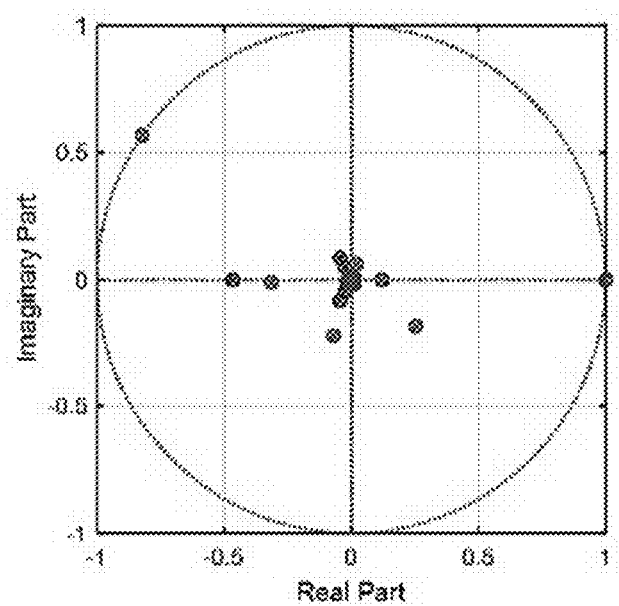
Fig. 4

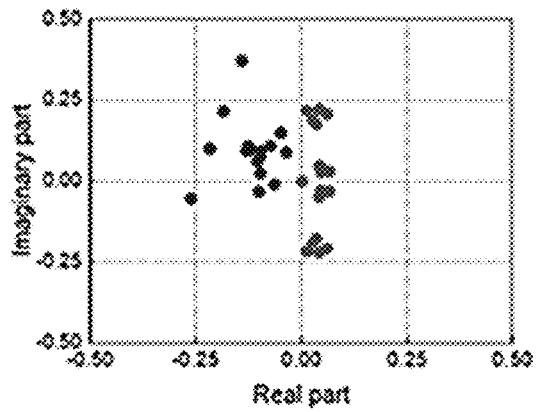 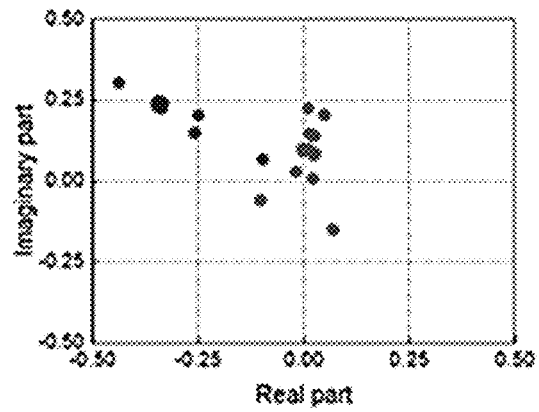
Fig. 6A  Fig. 6B
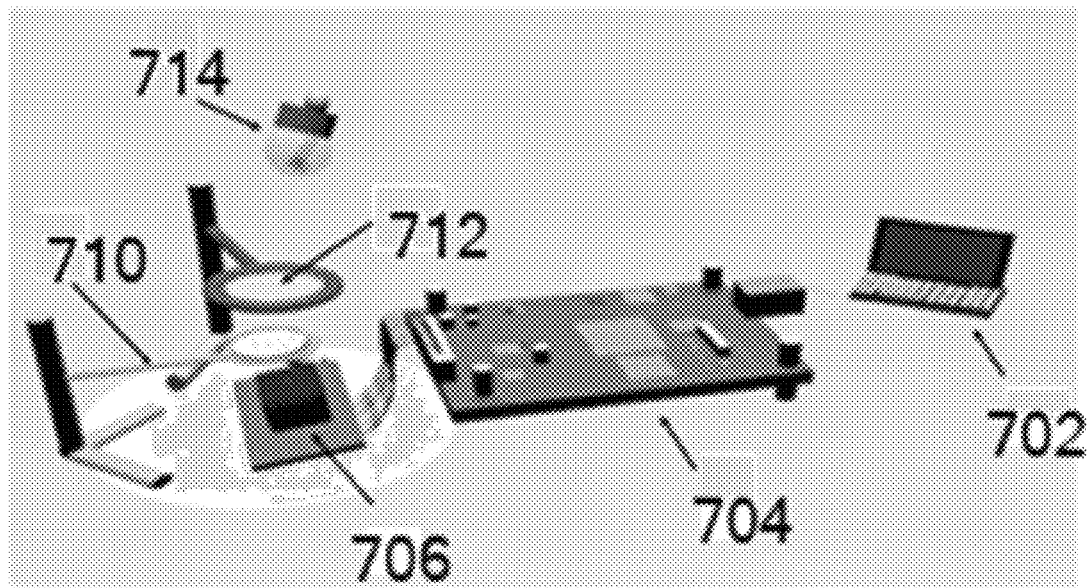
Fig. 7

SYSTEM AND PARAMETRIC METHOD FOR CANCER DISCRIMINATIONS

CROSS-REFERENCE TO RELATED APPLICATIONS AND PRIORITY

This patent application is a divisional of U.S. patent application Ser. No. 16/928,620 filed Jul. 14, 2020. This patent application is herein incorporated by reference in its entirety.

FIELD OF THE INVENTION

The present invention relates to a method and system for cancer cell discrimination, and more particularly a method combining optical measurements and statistical techniques for early cancer detection.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

It is crucial for diagnosing diseases such as cancer at an early stage. Although the symptoms of cancer are not apparent at the initial stage, if cancer spreads, effective treatment is a grueling task and, generally, the patient's survival rate is very low. When diagnosed at an advanced stage, more than 90% of women with breast cancer have been found to survive the disease for 10 more years compared to less than 20% of women surviving for 5 years. Approximately 93% of patients diagnosed with colon cancer and detected at an early stage have 5-year survival rates compared to those diagnosed at a later stage. A similar increase in survival rate is found for other types of cancer when detected early. Accordingly, in the past two decades, extensive research has been carried out to develop various means that aid in the efficient classification of normal and cancer cells. The classification of normal and cancer cells is very important because it assists in early detection of cancer and thereby helps cancer patients to receive better treatment and improve their chances of survival.

Considering traditionally employed methods, Mukhopadhyay et al. used the Empirical Mode Decomposition (EMD) technique for detecting cancer at an early stage. The signals obtained from elastic scattering spectroscopy from the normal and cancer cells are processed using the EMD technique. The optical signal response is decomposed into a set of finite numbers of band limited signals known as the intrinsic mode function (IMF). The area parameter of each IMF obtained for normal and cancer cervical tissues is used as a tool for discriminating the tissues. The results show that the algorithm is efficient in sorting normal and cancerous tissues. However, EMD has limitations in discriminating the components in narrowband signals. Li et al. applied a genetic algorithm (GA) combined with linear discriminant analysis (LDA) as a signal processing technique in the detection of nasopharyngeal cancer. The spectra obtained from surface-enhanced Raman Spectroscopy for malignant and benign tissues are analyzed using the GA-LDA method. The alterations in the features of the Raman spectra of normal and cancer tissues are used for differentiating the tissues. The GA-LDA algorithm is utilized to look for the dominant features of the spectra. The algorithm, although it worked efficiently for cancer tissue discrimination based on feature selection, has limitations. The algorithm has to be run more than 100 times to select the appropriate spectral bands. The overall accuracy of the diagnostic model is 76.9%. Li et al. used the same (GA-LDA) technique for detecting bladder cancer. As mentioned earlier, the downside of this technique is that the algorithm is executed more than 100 times and Raman variables are searched for characterizing bladder cancer in each run.

Duraipandian et al. reported the use of GA along with partial least squares-discriminant analysis (PLS-DA) with double cross-validation (dCV) for the feature selection from Raman spectra of normal and cancerous cervical tissues. The results show a diagnostic accuracy of 83% in discriminating cancerous and normal cervical tissues. Franceschini et al. applied a projection image transformation algorithm for processing images of breast tissues. The optical images processed by this technique enhance the features that show the inhomogeneity in normal and cancerous tissues. The spatial resolution of the optical method used in this work is 1 cm but they can detect tumors of smaller size if the images have good optical contrast. Salomatina et al. have investigated the optical differences between cancerous and normal skin cells. They have utilized a sphere spectrophotometer to conduct the absorption and transmittance measurements. Optical properties such as absorption and scattering coefficients of the normal and cancer skin are obtained from the measured quantities using a quasi-Newton inverse algorithm and the Monte Carlo technique. The efficiency of the quasi-Newton inverse algorithm is that it requires many fewer iterations (less than 10) to reach convergence. The optical parameters obtained are statistically acceptable if the probability value is less than 0.05, which means the optical properties of the normal and cancer tissues differ by more than 95%.

The Prony technique, introduced in 1795 by Gaspard de Prony to describe gas expansion, is a well-known signal analysis technique. It has wide application in signal processing in the biomedical field. In biomedical signal processing, the Prony technique is prominently used for the characterization of tumors, for cancer detection and for power spectrum estimation of DNA sequences. Hauer employed the Prony method for determining the modal components of the signal response obtained from a Western U.S. power system. The signal components extracted using the Prony technique—in combination with Fourier techniques and frequency domain approaches—are used for dynamic modeling of the power system. The results show that the Prony algorithm gave a good fit with a reasonable SNR value for the high noise signal. The Prony method is used for finding low frequency oscillations in power systems. Xiao et al. compared the Fourier Transformation (FFT) technique and the Prony technique in their study identifying low frequency oscillations in power systems and concluded that Prony is a competent technique compared to FFT. The simulation results show that the technique is efficient for identifying low frequency oscillations in real grids.

Chuang et al. applied the Prony analysis technique on a synthesized signal that represents the backscattered signal from radar targets. Further, the Prony algorithm is used to deduce natural resonances of the targets. The resonances obtained using the Prony method are used for target detection and discrimination. It was concluded that the results obtained through the Prony method in the absence of noise are more reliable than those from the numerical search procedure. The lengthy computation time in numerical search methods is greatly overcome by using Prony's method. Marple et al. discussed the use of Prony's method to detect and classify acoustic transient signals obtained from subaquatic sonar sensors. The energy component coupled to the pole amplitude and damping constants of the estimated model is used as a key for transient detection and for extraction of features used in classification. The results show that the technique worked very well even in the presence of noise in the signal.

Furthermore, the Prony algorithm is widely used in biomedical signal processing for tumor detection. Huo et al., in an attempt to model breast tumors, reported the use of the Prony method. The tumor in the breast is represented as a concealed dielectric target. When it is subjected to a short EM pulse, it backscatters a signal that includes complex natural resonances (CNR), which is equivalent to the poles of the tumor. The Prony method gives the poles and residues from the time domain backscattered signal. The complex natural resonance can be correlated with the morphological and intrinsic composition of the tumor. Hence, the optical and electrical properties can be used to detect and identify tumors. Li et al. utilized an approach similar to for characterizing breast tumors based on 2D-FDTD simulation. The time-domain response of the tumors is obtained through FDTD simulation and is analyzed using the Prony technique for characterizing the tumors. The results are promising in characterizing breast tumors when used in combination with imaging diagnosing methods such as ultrasound imaging, confocal microwave imaging and so on.

Wang et al. discussed the use of the Prony technique for extraction of poles from noisy data for tumor characterization. The results show that the poles extracted using the Prony technique gave accurate results even when the detected signal was mixed with a limited level of noise. Bannis et al. employed the Prony technique for breast cancer tumor detection from a scattered field electromagnetic (EM) signal. The poles extracted from the scattered EM signal are used as a tool for breast cancer detection. In another work to study the effect of the chest wall on breast tumor detection, the Prony algorithm was utilized for poles extraction. Gale et al. utilized the Prony method for estimating parameters of a nuclear magnetic resonance (NMR) signal obtained from blood plasma for the early detection of cancer. Roy et al. suggested a method to estimate the power spectral density of a DNA sequence. In this approach, the simulation results from Prony's all-pole model efficiently distinguished the coding and noncoding regions of a DNA sequence.

Conventional cancer screening techniques based on clinical studies are mostly invasive. Furthermore, these techniques require large amounts of samples, biomarkers, antigens, and antibodies. Biomarkers are molecules that are present in blood, urine, stool, tissues, or other bodily fluids that indicate normal or abnormal processes in the body. Cancer biomarkers include substances produced by the cancer cells or by other cells reacting to the cancer cells in the body. These biomarkers are helpful in detecting and diagnosing cancer cells. However, an important downside of these techniques is that repeated biopsies are required if the false positive rate is high. As a result, the emphasis on the development of reliable, label-free methods is growing inside the research community.

A non-invasive discrimination method of cancer cells from normal cells in a corresponding adherent culture has been introduced utilizing their cell morphology. The analysis of the corresponding intracellular distribution phase-shift data has been used to develop cancer index as an indicator to be utilized to distinguish the cancer from normal cells. On the other hand, cancer and normal cells were discriminated based on their biomechanics characteristics. The cellular properties were probed at the single cell level using atomic force microscopy (AFM). The corresponding elastic properties were measured with a proper designed indentation experiments. The extracted Young's modulus that represents the cellular deformability can be used quantitatively to distinguish the normal form cancer. Chromatography-mass spectrometry based on gas or biomarkers has been used for the metabolomics profiling of cells. With the help of multivariate analysis, a panel of metabolites revealed that was possible to discriminate cancerous from normal cells.

Electrically, a set of extracted parameters from the measured capacitance-voltage profiles has been used to recognize cancer from normal cells. The normal cells exhibit higher dielectric constants compared to cancer cells from the same tissue. On another study the electrical impedance spectroscopy has been employed to classify between normal and cancerous mammalian cells. Set of features allowed the classification of the samples in normal or cancerous with 4.5% of false positives and no false negatives. The interactions between cell compositions and light were used to discriminate and identify several types of cancer and normal cells. Empirically, the cancer cells exhibit higher transmittance intensity when compared to normal ones from the same tissue type. Artificial intelligence and deep learning techniques and method have proven to show an outstanding performance and capabilities in resolving recognition and classification problems. A combined deep learning approach in conjunction with expert trained data system was very powerful tool to identify cancer from gene expression data. Moreover, it can also contribute towards the understanding the complex nature of cancer based on large public data as well.

Accordingly, there exists a need for a system or method for early detection of cancerous cells from an organ tissue, which overcomes the drawbacks of the above elaborated traditional methods.

SUMMARY OF THE INVENTION

Therefore it is an object of the present invention to propose a method and system for cancer cell discrimination, and more particularly a method combining optical measurements and statistical techniques for early cancer detection.

The invention discloses a label-free method of detection of cancerous cells from an organ tissue, the method including the steps of extracting a plurality of cells from the organ tissue, observing and measuring optical transmission characteristics of the plurality of cells using a spectrophotometer, modeling the measured optical transmission characteristics using a statistical algorithm and calculating a figure of merit (FOM) for the plurality of cells, wherein the FOM is calculated from pole coefficients and locations corresponding to the plurality of cells.

In an embodiment of the present invention, the method further includes extracting a plurality of data parameters from the modelled optical transmission characteristics and processing the extracted data parameters to obtain the pole coefficients and locations corresponding to the plurality of cells.

In another embodiment of the present invention, the plurality of cells extracted from the organ tissue are suspended in a cell culture medium.

In another embodiment of the present invention, the measured optical transmission characteristics comprise reflection, absorption and variable attenuation parameters.

In another embodiment of the present invention, modeling of the measured optical transmission characteristics comprises fitting the measured optical transmission characteristics with a sum of decaying exponential signals using Prony algorithm.

In another embodiment of the present invention, the measured optical transmission characteristics are reconstructed using the Prony algorithm with a pre-defined fitting order.

In another embodiment of the present invention, an Autoregressive (AR) modeling technique is used to model the measured optical transmission characteristics of the plurality of cells.

In another embodiment of the present invention, analysis of variance (ANOVA) statistical approach is incorporated for determining significant AR coefficients, and poles are extracted from the determined significant AR coefficients, to provide a demarcation for cancerous cells.

In another embodiment of the present invention, variations in optical transmission characteristics of the plurality of cells are observed, due to differences in cell composition and intrinsic characteristics between normal and cancerous cells.

In another embodiment of the present invention, different coefficients and locations are observed for the plurality of cells, due to differences in cell composition and intrinsic characteristics between normal and cancerous cells.

In another embodiment of the present invention, the FOM is defined as FOM $(p)=C(p)/L(p)$, where $C(p)$ and $L(p)$ represent the pole coefficients and locations respectively, for the suspended plurality of cells.

In another embodiment of the present invention, pole quality (Q) is used as a figure of merit (FOM).

As another aspect of the present invention, a system for detection of cancerous cells from an organ tissue is disclosed, including a plurality of cells extracted from the organ tissue, a light source for directing light through the plurality of cells, an image sensor for detecting and measuring optical transmission characteristics of the plurality of cells, modeling the measured optical transmission characteristics using a statistical algorithm and calculating a figure of merit (FOM) for each of the plurality of cells, wherein the FOM is calculated from pole coefficients and locations corresponding to the plurality of cells.

In another embodiment of the present invention, the plurality of cells extracted from the organ tissue are suspended in a cell culture medium.

In another embodiment of the present invention, the image sensor detects and converts absorption, variable attenuation and reflectance, caused by the light source passing through the plurality of cells into electrical signals.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

FIG. 2A depicts amplitude, FIG. 2B depicts damping factor, FIG. 2C depicts frequency and FIG. 2D depicts phase, in accordance with the present invention.

FIG. 3A depicts Z-plane plot (unit circle) showing coefficients (in blue) and locations of poles (in red) for HeLa cell suspensions, in accordance with the present invention.

FIG. 3B depicts Z-plane plot (unit circle) showing coefficients (in blue) and locations of poles (in red) for 293T cell suspensions, in accordance with the present invention.

FIG. 4 depicts an extracted figure of merit (FOM) for 293T and HeLa, in accordance with the present invention.

FIG. 5A shows the FOM for lung normal, FIG. 5B shows the FOM for lung cancer, FIG. 5C shows FOM for liver normal and FIG. 5D shows the FOM for liver cancer, in accordance with the present invention.

FIG. 6A depicts figure of merit distributions for lung normal and cancer cells in accordance with the present invention.

FIG. 6B depicts figure of merit distributions for liver normal and cancer cells, in accordance with the present invention.

FIG. 7 is a schematic for the experimental setup, in accordance with the present invention.

DETAILED DESCRIPTION OF THE INVENTION

Figure 1A:
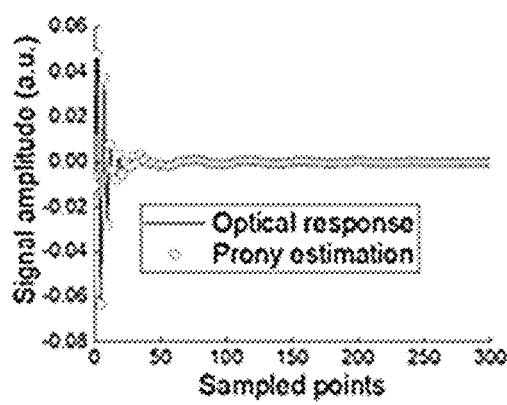
FIGS. 1A and B depict measured optical transmittance response of HeLa cells and 293T cells fitted with Prony estimations, in accordance with the present invention.
Figure 1B:
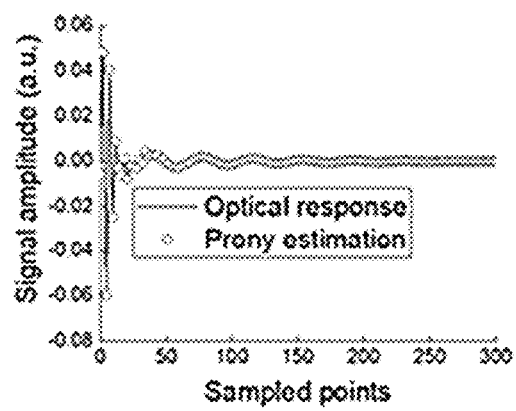

The aspects of a method and system for the discrimination of normal and cancer cells at an early stage, according to the present invention will be described in conjunction with FIGS. 1-11. In the Detailed Description, reference is made to the accompanying figures, which form a part hereof, and in which is shown by way of illustration specific embodiments in which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

The main objective of the proposed invention is for the discrimination of normal and cancer cells at an early stage. Various methods and techniques, such as the empirical mode decomposition technique, a genetic algorithm, a projection image transformation algorithm, a quasi-Newton inverse algorithm, and the Prony technique have been utilized for distinguishing normal and cancer tissues or cells. Label-free methods based on electrical, mechanical, optical, and biochemical cancer cell detection techniques have been reported in the research literature. The analysis of electrical, mechanical, and optical responses of cells combined with numerical methods is gaining popularity due to their improved efficiency in distinguishing between normal and cancer cells. Several signal processing algorithms such as prony, the matrix pencil method, and empirical mode decomposition, as well as modeling techniques such as autoregressive (AR), autoregressive moving average (ARMA), and autoregressive integrated moving average (ARIMA) are used to classify normal and cancer cells.

A preferred embodiment of the present invention combines advancement in optical measurements and Prony techniques to enhance the label-free based classification of cells based on their measured optical profiles. In an embodiment, six kinds of cells, HeLa, 293T, lung—cancer and normal, and liver—cancer and normal, are suspended in a cell culture medium or their corresponding media and respective transmission characteristics are collected. The cell lines under investigations—HeLa, 293T, lung and liver cells are taken from different tissue organs. However, the lung (as well as liver) healthy and cancer cell lines are taken from the same organ tissue. The transmission profiles are then fitted with a sum of decaying exponential signals using the Prony algorithm. A figure of merit is introduced, whose distribution in the complex z-plane plays a major role in the classification of cell type. The alteration in the values of FOM is due to the changes in cell composition and intrinsic characteristics of different cells.

The cell lines used in the present invention are procured per the American Tissue Culture Collection (ATCC) standard. Each type of cell is cultured in a medium that is specific for the cell type. Based on the type and feature of cells, the nutritional requirements for its growth in vitro also differ. This difference in nutritional requirements is applicable for normal and cancerous cells of the same tissue. A summary of the cells used in the present invention is shown in Table 1.

TABLE 1

| | CELL MODEL | TISSUE | CELL TYPE |
|---|---|---|---|
| 1 | BEAS 2B | Lung | Normal |
| 2 | HCC-827 | Lung | Cancerous |
| 3 | THLE2 | Liver | Normal |
| 4 | HEP G2 | Liver | Cancerous |
| 5 | HEK 293T | Kidney | Normal |
| 6 | HeLa | Cervical | Cancerous |

In an embodiment, a humidified air ambience with 5% carbon dioxide ($CO_2$) at 37° C. is maintained for all the cells. Considering BEAS 2B—normal lung cells, as per the ATCC guidelines, the culture plates on which the cells were cultured are precoated with a precoating mixture. The mixture used for BEAS 2B cells contains fibronectin (0.01 mg/mL), bovine collagen (0.03 mg/mL) and bovine serum albumin (0.01 mg/mL) diluted in bronchial epithelial basal medium (BEBM). Supplements such as penicillin (100 units/mL) and streptomycin (100 mg/mL) are added to the medium. For trypsinization, an EDTA solution (0.53 mM) with 0.5% polyvinylpyrrolidone (PVP) is used. Considering HCC-827—lung cancer cells, the ATCC-recommended medium suitable for culturing CC-827 lung cancer cells is the Roswell Park Memorial Institute (RPMI) 1640 medium. The medium is suitable for culturing a variety of mammalian leukemic cells. The medium possesses a 10% heat-inactivated fetal bovine serum (FBS) supplement as base. The trypsinization of the cells is done with 0.25% trypsin (a 0.53 mM EDTA solution).

Considering THLE2—normal liver cells, a mixture consisting of 2.9 mg/mL of collagen I, 1 mg/mL of fibronectin, and 1 mg/mL of bovine serum albumin in BEBM is used as a precoating mixture coated on the culturing plates. The supplements for the media are heat-inactivated FBS (HyClone™, US—10%) and penicillin-streptomycin (Gibco—1%). Trypsinization is carried out with 0.5% trypsin (0.53 mM EDTA solution). Considering HEPG2—liver cancer cells, the HEPG2 cancer cells from liver tissue are grown in Dulbecco's modified Eagle's medium (DMEM—HyClone™) in culture plates. Ten percent of FBS (HyClone™, US) and 1% of penicillin-streptomycin (Gibco) are supplements for the medium. Per ATCC guidelines, trypsinization for these cells is done using 0.5% trypsin (0.53 mM EDTA solution). Considering 293T—normal kidney cells, these normal cells from kidney tissue are cultured in DMEM (HyClone™) base. The medium is supplemented with 10% FBS and antibiotics such as penicillin-streptomycin and gentamicin. Considering HeLa—cervical cancer cells, according to the ATCC standard, the HeLa cells are cultured in DMEM (HyClone™) with 7% fetal calf serum (FCS) and the antibiotics PenStrep and gentamicin as supplements; this cell line best displays the relationship between the input-output signals. The cells are sub cultured and trypsinized as per the ATCC protocol. Each type of cell is suspended and cultured separately.

The transmission profile of the cells is measured using a JASCO (V-670) spectrophotometer. A light beam from a xenon light source is split into its component monochromatic beams by diffraction grating. The single wavelength beam is divided into two equal-intensity beams. One of the two beams is the reference beam that passes through a cuvette loaded with only the media. The second beam passes through a transparent container loaded with cells in the media. The container is a high precision cell made of quartz superasil with light path of 1 mm and an area of 2 by 2 $mm^2$. The spectrometer has an electronic detector that measures the intensities of the light beam. Based on the measured intensities, the transmittance of the cells is determined. Considering the sensor and light source, Mini-Spectrometers C11708MA are employed, and the optical sensor used, converts variable attenuation or reflectance into signals.

In accordance with the present invention, the measured optical responses are fitted or modeled with a sum of damped exponential signals as given in equation (1):

$$y[n] = \sum_{i=1}^{P} A_i e^{j\theta_i} \cdot e^{(\alpha_i + j2\pi f_i)T_s(n-1)}; \quad n = 1, 2 \ldots N \quad (1)$$

where N is the number of samples, and p is the order of the fitted model, which is same as the total number of damped exponential components in the summation. The least number of exponentials that gives the best fitting is considered the optimum order of the fitted model. The complexity of the fitted model increases with the increase in the order number. The $i^{th}$ exponential component has amplitude $A_i$ (same unit as y[n]), frequency $f_i$ (Hz), damping factor $\alpha_i$ (per second), and initial phase $\theta_i$ (in radian). $T_s$ is the sampling interval between consecutive data samples. Using Z-transformation, equation (1) is expressed as follows:

$$y[n] = \sum_{i=1}^{P} h_i z_i^{n-1} \quad (2)$$

where $h_i$ represents the coefficient (magnitude) of the estimated poles and $z_i$ denotes the location of the poles. These parameters are expressed as:

$$h_i = A_i e^{j\theta_i} \quad (3)$$

$$z_i = e^{(\alpha_i + j2\pi f_i)T_s} \quad (4)$$

The sampled data is preprocessed prior to fitting and parameter extraction. The first step in preprocessing is to eliminate noise from the data. This is done by smoothing the data. Data smoothing is followed by data detrending to remove trends, if any, from the measured sequence. The detrending operation gives a more accurate linear model that best describes the relationship between the input-output signals. Based on the observation of the pole coefficients and locations, a figure of merit (FOM) is introduced for the discrimination between normal and cancer cells from the same tissue.

In an embodiment of the present invention, six types of cells are utilized. In addition to these cell lines, the HeLa and 293T cells are utilized to carry out the proposed current approach in terms of detection capabilities. Normal and cancer cells of lung and liver are both used to demonstrate cell identification. The normal and cancer cells are taken from same tissues. Using a hemocytometer, the cell concentration in each suspension is adjusted to $10^7$ cells per mL with 5% mean error. Subsequently, each type of cell suspension is loaded in the experimental setup and the optical transmission of the cells is measured over the wavelength of 590-1093 nm with a spectral resolution of 20 nm. The recorded transmittance of the responses, after de-embedding the media and holder contributions, are sampled with a step of 2.3 nm. The de-embedding of the media and holder contributions are then performed by subtracting the suspension responses directly from the filled control medial response.

Figure 2A:
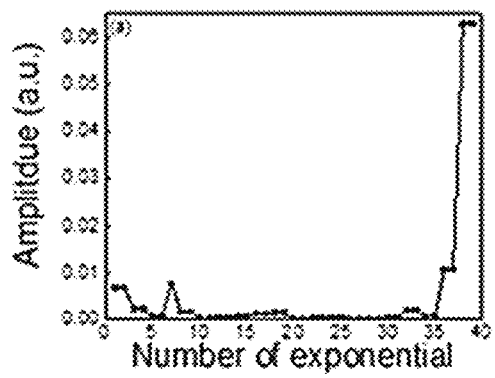
FIGS. 2A-2D depict extracted parameters versus number of exponentials in the fitted model for 293T cell line.

FIGS. 1A and B of the present invention show signal intensities varying with wavelength (i.e., measured optical transmittance response of HeLa cells and 293T fitted with Prony estimations. The measured transmittance is sampled at a uniform sampling interval of Ts=2.3 nm. This results in a number of samples of N=256). As the measured signal exhibits transient behavior, a wavelength modified Prony algorithm can be applied. FIGS. 2A and B depict the measured optical response superimposed with the Prony estimated signal for the HeLa and 293T cell lines, respectively. The least number of exponentials that gives the best fitted model is considered the optimum order of the model. The optimum order (p) is 40, which is the minimum required order that provides the excellent fitting. A higher order (higher p values) result in redundancy and require further processing resources. It is recommended to apply the same order to both the 293T and HeLa cell suspensions for fair comparison. Parameters such as amplitude, frequency, phase and damping factor of the exponentials are extracted from the fitted response of each type of cell.

Figure 2B:
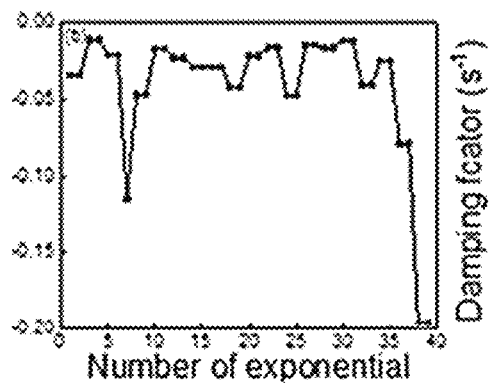
Figure 2C:
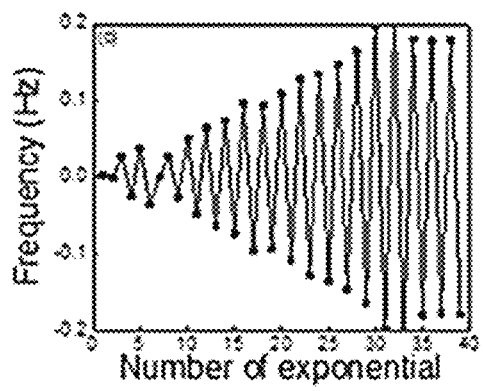
Figure 2D:
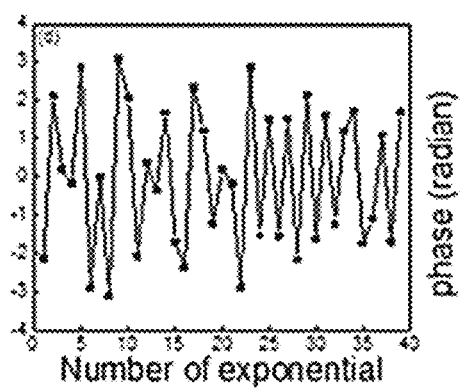
Figure 5A:
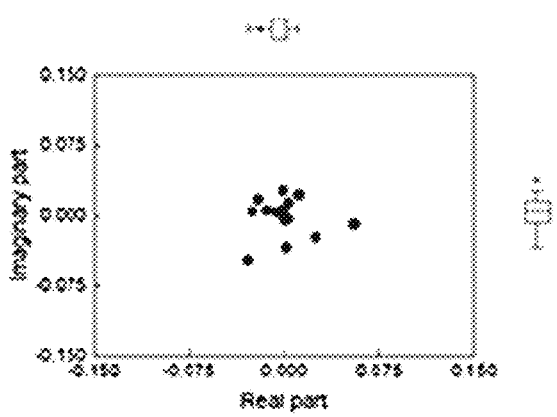
FIGS. 5A-5D depict the extracted figure of merit (FOM) for normal and cancer cell lines from same tissue.
Figure 5B:
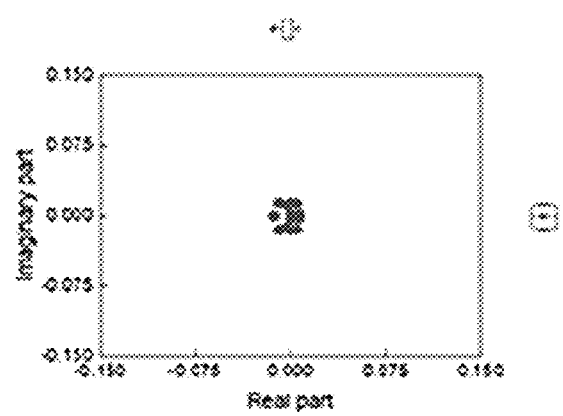
Figure 5C:
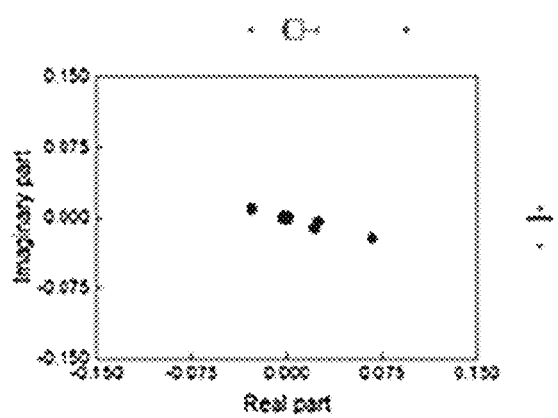
Figure 5D:
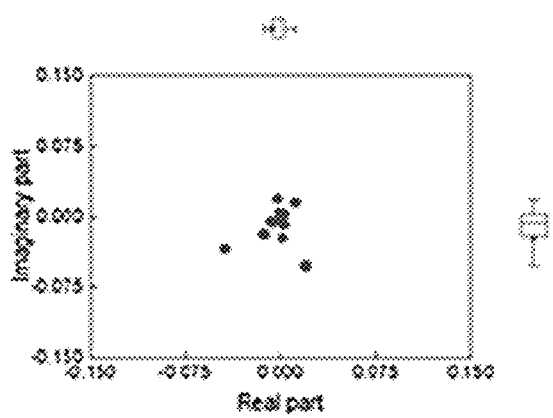

FIG. 2A to 2D graphically show the plots of amplitude, damping factor, frequency and phase, respectively, obtained for 293T with a fitting order of 40. FIG. 2A depicts amplitude, FIG. 2B depicts damping factor, FIG. 2C depicts frequency and FIG. 2D depicts phase, in accordance with the present invention. The measured data are smoothed using the Savitzky-Golay method. This is used to increase the data precision without distorting the signal tendency. The extracted parameters are further processed to extract the corresponding coefficients and pole locations. The coefficients and locations of poles are computed using equations (3) and (4). The extracted coefficients and location of poles for the HeLa and 293T cell suspension are illustrated in FIGS. 3A and 3B, respectively. FIG. 3A depicts Z-plane plot (unit circle) showing coefficients (in blue) and locations of poles (in red) for HeLa cell suspensions, in accordance with the present invention. FIG. 3B depicts Z-plane plot (unit circle) showing coefficients (in blue) and locations of poles (in red) for 293T cell suspensions, in accordance with the present invention. A review of Prony's method regarding the signal approximation is conducted using MATLAB code. Rodríguez's algorithms and codes are adopted in the present invention.

As illustrated in FIGS. 3A and B, the extracted poles are located within the unit circle of the z-plane. The y-axis represents the imaginary part and the x-axis represents the real part. The coefficients of 293T are focused around the origin point when compared to HeLa in the z-plane. Considering that the distribution of the coefficients and poles locations is not very helpful to be used for cell identification, a figure of merit (FOM) is introduced for better identification accuracy. The FOM is defined as follows:

$$FOM(p) = C(p)/L(p) \quad (5)$$

where $L(p)$ and $C(p)$ represent the location and coefficients of the poles, respectively. The computed FOM is then normalized for each type of cell with its corresponding maximum value. FIG. 4 illustrates the FOM for both HeLa and 293T cell lines. The FOM for the HeLa distribution is very close to the center of the unit circle compared to the 293T distribution. Although the Prony algorithm was developed for modeling signals in the time domain, it can be applied for responses obtained in frequency domains as well (in conventional methods, the poles have been extracted directly from the frequency response using a technique that is analogous to Prony).

FIG. 4 shows the extracted FOM for HeLa and 293T cells. The FOM for the HeLa distribution is very close to the center of the unit circle. Significant differences in cell composition for normal and cancer cells have been reported. Their interaction with light cause a change in the optical absorption and transmission response. Due to differences in the composition of the different type of cells, the light interaction with the cells causes an alteration in their optical and transmission response. The modifications of the optical response from normal to cancer are explained mainly by morphological changes, modification of its physiological and biochemical properties that affect the refractive index and allow them to be differentiated from each other. The pole locations and coefficients are affected accordingly. As tested experimentally, cancer cells exhibit higher transmittance intensity when compared to normal ones from the same tissue type. The FOM is proportional inversely with $L(p)$ and therefore, for corresponding high coefficients, lower FOM values are obtained. Further, the complex poles are defined as $\sigma \pm j\omega$, where $\sigma$ is the damping coefficient and $\omega$ is the resonant pulsation. The damping and resonant poles are smaller in cancer cells compared to normal cells. Therefore, the FOM becomes smaller for cancer cells than for normal cells.

Based on these results, it is shown that coefficients and pole locations vary with composition and cell morphology and the main difference between normal and cancer cells of the same tissue is in terms of composition and morphology. Hence, the proposed FOM is a distinctive parameter that can be used to explore the detection and identification of normal and cancer cells. This is possible when the technique is used only for fitting the response in the frequency domain to the sum of the damped exponential and for parameter extraction. The objective here is to make inferences from the obtained parameters and for further processing. The present invention demonstrates the validity of using the Prony technique to model a frequency domain signal, as the extracted parameters are used for making inferences for cell identification— and thereby making it possible to classify normal and cancerous cells for the same tissue.

Therefore, the FOM for lung and liver normal and cancerous suspensions are extracted per the introduced procedure and are depicted in FIG. 5. FIG. 5 depicts the extracted figure of merit (FOM) for normal and cancer cell lines from same tissue. FIG. 5A shows the FOM for lung normal, FIG. 5B shows the FOM for lung cancer, FIG. 5C shows FOM for liver normal and FIG. 5D shows the FOM for liver cancer, in accordance with the present invention. The distribution of the FOM is closer to the origin when compared with the normal distribution. Each plotted measurement represents the average of 15 measurements. The multiple measurements are conducted on different aliquots taken from the same sample suspension in the same region spot. The error bars in the subfigures of FIG. 5 represent the average values along with maximum and minimum values. The bar corresponding to the x-axis represents the average in the FOM real part, while the endpoints represent its maximum and minimum values. The bar corresponding to the y-axis represents the average in the FOM imaginary part, while the endpoints represent its maximum and minimum values. For further investigations, the distribution of the FOM for normal and cancer cells are superimposed on each other, as depicted in FIG. 6.

FIG. 6A depicts figure of merit distributions for lung normal and cancer cells in accordance with the present invention. FIG. 6B depicts figure of merit distributions for liver normal and cancer cells, in accordance with the present invention. FIG. 6A superimposes the FOM of the lung normal and cancer corresponding FOMs. FIG. 6B superimposes the FOMs for the liver normal and cancer cell lines. A majority of the real part of the cancer corresponding poles is located in the right hand (side) of the plot, and a majority of the real part of the normal corresponding poles are located in the left hand (side) of the plot.

The figure of merit (FOM) proposed in the present invention correlates the location of the poles (L(p)) and C(p)) the locations and coefficient of poles. Scientifically, significant differences in cell composition for normal and cancer cells have been reported, and hence, their interaction with light will cause a change in the optical absorption and transmission response. Due to differences in the composition of the different type of cells, the light interaction with the cells causes an alteration in their optical and transmission response. The modifications of the optical response from normal to cancer state are explained mainly by morphological changes, modification of its physiological and biochemical properties that affect the refractive index and allowing them to be differentiated from each other. The poles location and coefficients will be affected accordingly. Therefore, if 85% of the FOM values result to be located in the right hand of the Z-plan—then the cell lines under study is considered to be cancer, else it is normal. There is a clear discrimination strategy—by performing optical measurements on the different in vitro cell normal and cancer cell line models, the developed data processing procedure based on the Prony method works to achieve a label-free discrimination between cancer and healthy cells from the same tissue type.

The present invention addresses the classification and discrimination between normal and cancer cells from the same tissues. A label-free method combining the Prony estimation theory and optical transmittance measurements is introduced and proven to be a powerful technique. The proposed approach has been examined using four types of different cell lines. The measured optical responses are reconstructed using the Prony algorithm with same fitting order of 40. Based on the observations, a normalized figure of merit (FOM) is introduced for identification. Based on this merit, the distribution of the poles around the center of the unit circle of the normal cell lines is closer than the cancer cell lines from same tissues (in the case of lung and liver cells). These findings are considered the foundation stage for cell identification using optical measurements combined with the Prony estimation theory.

To plot the FOM, the following MATLAB code is developed. The function has two inputs, "a" and "b". "a" represents the computed figure of merit for the cancer cells, whereas "b" represents the computed figure of merit for the normal cells. The plot includes the unit circle for reference.
function [ ]=graphpronyayesha(a, b)
figure % for opening new figure to plot the FOMs data.
[hz1, hp1]=zplane(a,a), % plot the input "a" as a cross in the z plane.
grid on,% turn on grids
hold on,% Plot the second FOM (for the normal cells) graph in same figure
[hz2, hp2]=zplane(b,b), % plot the input "a" as a cross in the z plane.
hold off,
set(findobj(hz1, 'Type', 'line'), 'Color', 'b'), % color the input "a" in blue.
set(findobj(hp1, 'Type', 'line'), 'Color', 'b'), % color the input "a" in blue.
set(findobj(hz2, 'Type', 'line'), 'Color', 'r'), % color the input "b" in red.
set(findobj(hp2, 'Type', 'line'), 'Color', 'r'), % color the input "b" in red.

In another embodiment of the present invention, Autoregressive (AR) modeling techniques are used to fit a measured optical transmittance of both cancer and normal cells profiles. Analysis of variance (ANOVA) statistical approach is incorporated to determine the significant AR coefficients. The transmitted light intensity passes through the cells get affected by their intercellular compositions and membrane properties. In this embodiment—four types of cells lung—cancer and normal, liver—cancer and normal cells are suspended in their corresponding media and their transmission characteristics are collected and processed. The AR coefficients of each type of cell are analyzed with the statistical technique ANOVA, which provided the significant coefficients. The poles extracted from the significant coefficients provide an improved demarcation for normal and cancer cells. These outcomes can be further utilized for cell classification using statistical tools.

The four type of cells utilized in this embodiment of the present invention, is shown in Table 2. The cell lines are processed according to the standards established by the American Tissue Culture Collection (ATCC). The cells from two different cell lines (lung—normal and cancer and liver—normal and cancer) used in this embodiment are cultured with the corresponding culture medium.

TABLE 2

| | CELL LINE | TISSUE | CELL TYPE |
|---|---|---|---|
| 1 | BEAS 2B | Lung | Normal |
| 2 | CC-827 | Lung | Cancerous |
| 3 | THLE2 | Liver | Normal |
| 4 | HEP G2 | Liver | Cancerous |

FIG. 7 shows an optical measurement setup or experimental setup in accordance with the present invention, for measuring light transmission intensity. A laptop 702 equipped with HMSEvaluation software is used for measurements acquisition, an evaluation board (C113451-01) 704 is used for interface purpose. Other components included in the setup are an Image sensor (C11708 MA) 706, a sensor board (C113451-02), a sample holder 710, a Convex lens holder 712 and a Xenon light source 714. C11708 MA mini-spectrometer optical sensor 706 is placed under a host sample holder 710. High precision cell made of quartz superasil with light path of 1 mm (Hellma analytics/Germany) is used as the host sample holder. Each sample suspension is loaded inside the cell individually. The sensor board (C11351-02) output terminals are connected to the evaluation board (C113451-01) 704 to transfer data to a laptop 702. The collection of the light data and their corresponding processing are carried out through the Hamamatsu-Mini-spectrometer for MS 'HMSEvaluation' software installed on the laptop 702. A light xenon source (Xenoncorp/USA) 714 is used to direct the light towards the sample. The sensor 706 converts the photo-electrical light that passes through the sample and convex lens 712 to electrical signal.

Considering the principles of the AR model in accordance with the present invention, a set of N discrete data samples are expressed in the AR (p) model as given in equation (6):

$$x(n) = 1 + \sum_{k=1}^{P} a_k x(n-k) + e(n) \quad (6)$$

$a(0)=1$, $n=1, 2, 3 \ldots$, N where $x(n)$ is the present output, p represents the order of the model, and $a_k$ represents the AR coefficients. $e(n)$ represents the random shock or random noise and is assumed to be white Gaussian noise: $WN(0, \sigma^2)$. The all-pole model can be represented in the z domain as follows:

$$A(z) = (1 + a_1 z^{-1} + a_2 z^{-2} + \ldots + a_p z^{-P})^{-1} \quad (7)$$

A key feature of AR modeling is that it does not have any domain constraints. Any discrete signal, whether in time or frequency domain, can be modeled using an AR model. In addition, the signal may or may not have transients. Metrics such as prediction accuracy, mean square error (MSE), and final prediction error (FPE) are helpful in evaluating the performance of the model. The discrete dataset was preprocessed to remove noise and trend in the data. This was carried out by data smoothing followed by data detrending.

The Final Prediction Error (FPE) is utilized for the estimation of the model-fitting error and the use of the developed model to predict new outputs. The selected model should minimize the FPE, which indeed represents a balance between the number of parameters and the variations. The FPE measures the fit to estimated data, i.e. the model quality. The Final Prediction Error (FPE) is defined by the following equation:

$$FPE = \left(\frac{1+(d/N)}{1-(d/N)}\right) SSE \quad (8)$$

where SSE is the sum of square error, N is the number of values in the estimation data set and d is the number of estimated parameters. The mean-square error (MSE) measures how closely the predictors tracks the actual data. The MSE is frequently used in the analysis of variance, and is calculated as follows:

$$MSE = (x_{ia} - \hat{x}_1)^2 \quad (9)$$

where $x_{ia}$ is the actual data point and $\hat{x}_1$ is the average of the actual data set. The squaring is used usually to exaggerate the influence of outliers.
The SSE is then can be expressed as:

$$SSE = \sum_{i=1}^{N} (x_{ia} - \hat{x}_1)^2 \quad (10)$$

Figure 8A:
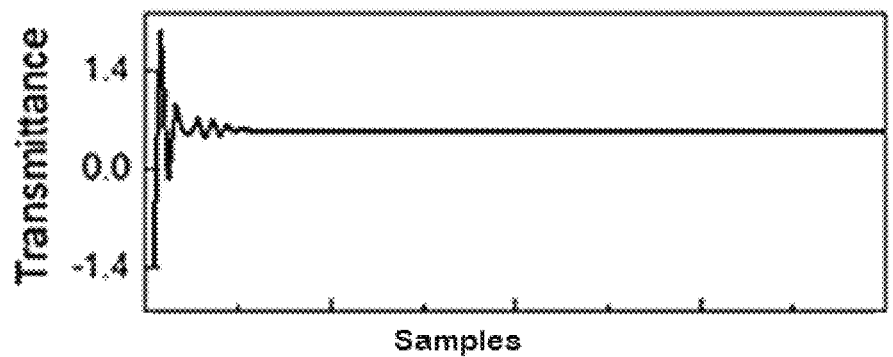
FIG. 8A shows measured optical transmittance response of a cancerous liver.
Figure 8B:
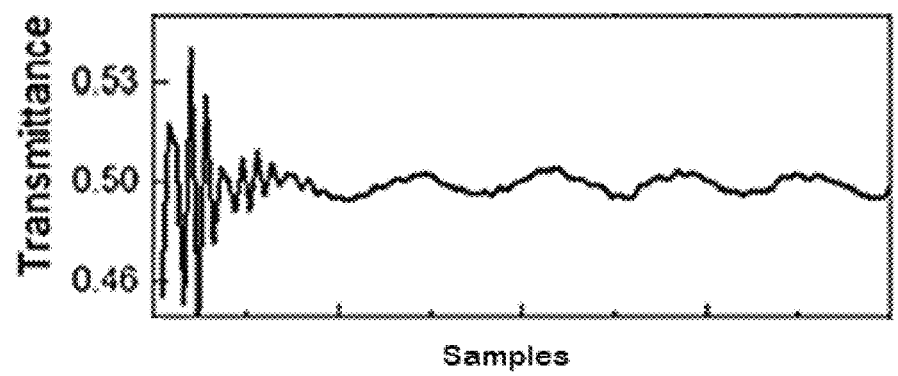
FIG. 8B shows measured optical transmittance response of a normal liver.
Figure 8C:
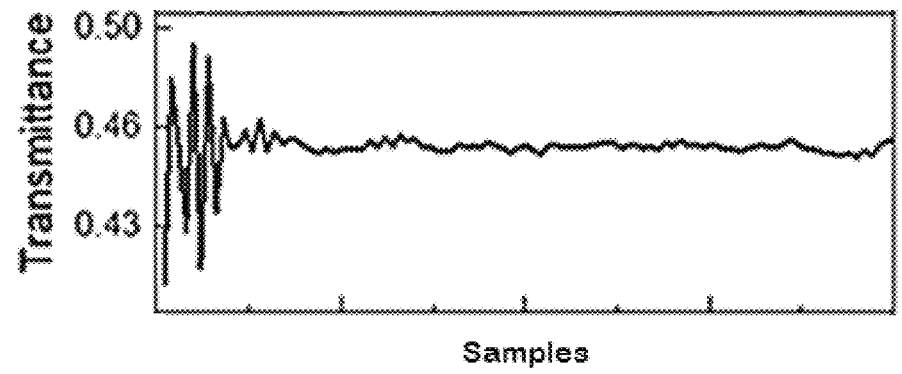
FIG. 8C shows measured optical transmittance response of a cancerous lung and FIG. 8D shows measured optical transmittance response of normal lung cells in accordance with the present invention.
Figure 8D:
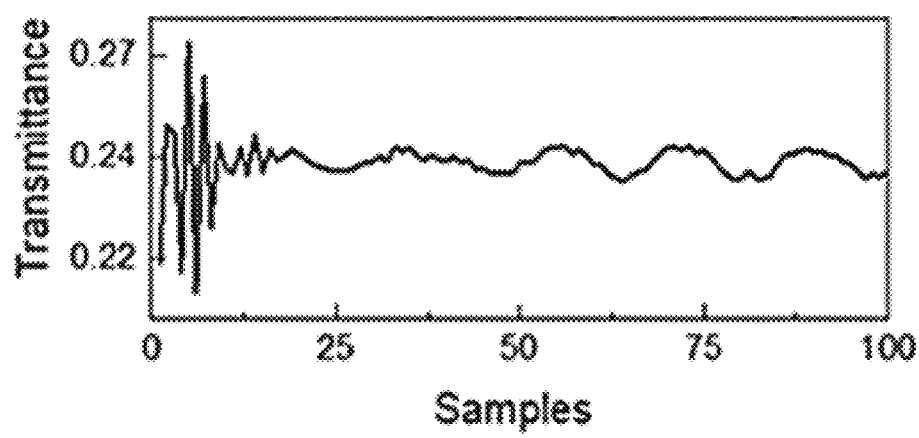

The F-statistic in ANOVA analysis that determine the significant of coefficients, mathematically can be expressed as follows:

$$F = MSA/MSE \quad (11)$$

where: MSA and MSE are the calculated mean of sum of all treatment squared errors and calculated mean of sum of squared errors, respectively. MSA and MSE are expressed as per follows:

$$MSA = SSA/(k-1) \quad (12)$$

$$MSE = SSE/(N-k) \quad (13)$$

where k total number of samples (treatments) being considered and N is the total number of observations (data points) available for all treatments. SSA and SSE are sum of squared errors of all treatment (sample) means vs grand mean and sum of squared errors of all observations vs respective sample means, respectively. The normal and cancer cells from the two cell lines (normal lung, cancerous lung, normal liver, and cancerous liver) are cultured separately. The norms of the ATCC are followed for the sub-culturing and trypsinization of the cells. The cell suspension preparation and culturing is done separately for each cell type. The suspension for each cell type contained 107 cells per mL. The cell count in the suspension of each type of cell is conducted using a hemocytometer with a 5% mean error. The suspension is then loaded in the experimental setup and the optical profile of the cells in the suspension is recorded. The measured transmission profile of the benign and malignant cells of the lung and liver tissues are shown in FIG. 8A to D respectively (which depicts measured optical transmittance response of a (a) cancerous liver, (b) normal liver, (c) cancerous lung, and (d) normal lung cells. FIG. 8A shows measured optical transmittance response of a cancerous liver, FIG. 8B shows measured optical transmittance response of a normal liver, FIG. 8C shows measured optical transmittance response of a cancerous lung and FIG. 8D shows measured optical transmittance response of normal lung cells in accordance with the present invention. The measured transmittance is sampled at a uniform sampling interval of Ws=2.3 nm).

TABLE 3

| Type of cell | Prediction accuracy | MSE | FPE |
| --- | --- | --- | --- |
| Normal lung | 91.61% | 5.72e−08 | 6.00e−08 |
| Cancerous lung | 90.75% | 1.13e−07 | 1.18e−07 |
| Normal liver | 93.48% | 6.53e−08 | 6.84e−08 |
| Cancerous liver | 99.76% | 6.59e−08 | 6.91e−08 |

Table 3 summarizes the metrics such as prediction accuracy, MSE, and FPE of the fitted AR model of each type of cell for an order 6. The complexity of the model increases with the order of the model. The AR model coefficients of order 6 obtained for the four types of cells are shown in Table 4. It is concluded that the coefficients are of different values for different types of cells. This reflects the alteration in the composition and intrinsic properties of the different cell types. Moreover, the normal and cancer cells from the same tissue have different coefficient values, implying the variation in their composition, morphology, and intrinsic properties.

TABLE 4

| AR Coefficients | Normal Lung | Cancerous Lung | Normal Liver | Cancerous Liver |
|---|---|---|---|---|
| $a_1$ | −0.16 | +0.06 | −0.13 | −0.68 |
| $a_2$ | −0.90 | −0.94 | −0.96 | −0.95 |
| $a_3$ | +0.03 | −0.23 | −0.08 | +0.43 |
| $a_4$ | +0.42 | +0.36 | +0.46 | +0.36 |
| $a_5$ | +0.05 | +0.12 | +0.13 | −0.09 |
| $a_6$ | +0.01 | +0.02 | +0.06 | −0.01 |

Table 5 shows the poles extracted for the normal and cancer cells of the lung and liver tissue used in this work. The poles can be real valued or complex conjugate pairs. For instance, the poles $P_1$ and $P_2$ of liver cancer cells are real and distinct, while their remaining poles ($P_3$-$P_6$) occur as complex conjugate pairs. All the extracted poles of lung (normal and cancer) cells occur as complex conjugate pairs.

TABLE 5

| Cell Type | $P_1, P_2$ | $P_3, P_4$ | $P_5, P_6$ |
|---|---|---|---|
| Normal lung | −0.687 ± 0.305i | −0.05 ± 0.16i | 0.820 ± 0.32i |
| Cancerous lung | −0.688 ± 0.309i | −0.15 ± 0.21i | 0.800 ± 0.24i |
| Normal liver | −0.71 ± 0.33i | −0.10 ± 0.32i | 0.88 ± 0.32i |
| Cancerous liver | −0.1 ± 0i, 0.35 ± 0i | −0.65 ± 0.23i | 0.87 ± 0.11i |

Figure 9A:
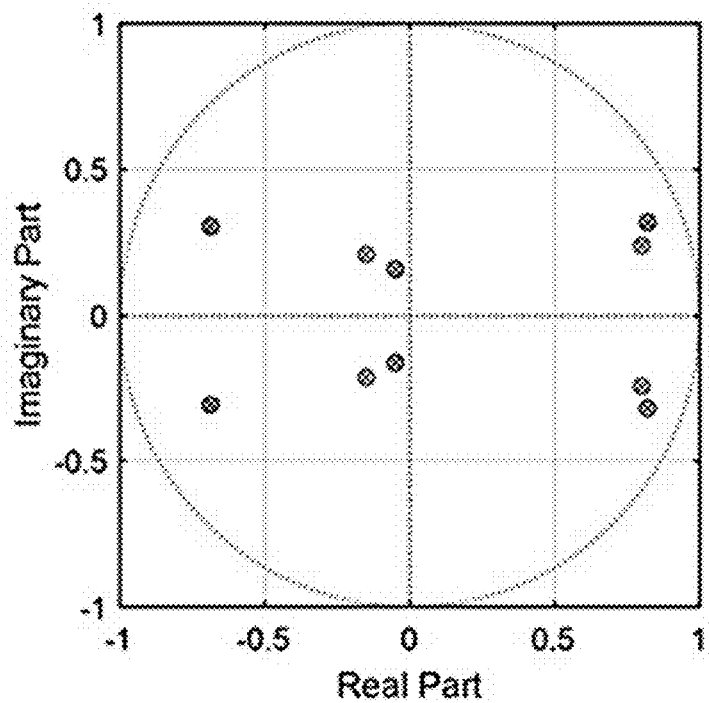
FIG. 9A depicts the distribution of poles of the normal and cancer cells of the lung and FIG. 9B depicts the distribution of poles of the normal and cancer cells of the liver in the z-plane.
Figure 9B:
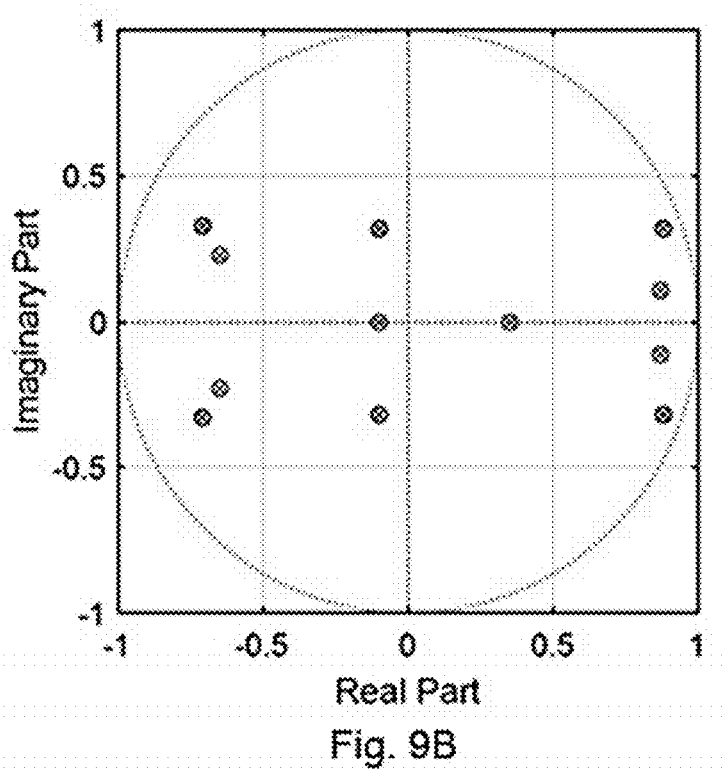

The distribution of the poles of the normal and cancer cells of the lung and liver in the z-plane is shown in FIGS. 9A and 9B, respectively. The poles of the normal cells are illustrated with blue dots whereas the red dots represent the poles of the cancer cells. As shown in FIG. 9, the poles of the different cells have different distributions in the z-plane. In addition, the distribution of the poles of the normal and cancer cells of the same tissue are also different. Any deviation from the pole values of the normal cells shows the presence of abnormalities.

The modifications of the optical response from normal to cancer state are explained mainly by morphological changes, modification of its physiological and biochemical properties that affect the refractive index and allowing them to be differentiated from each other. The poles location and coefficients are affected accordingly. The applied optical measurements conditions are not harsh to the cells. The applied light did not alter temperature of the cells. The O2 is dissolved in the media which helps the cells to survive. The pH is maintained—and not affected by light. The pH is measured before and after. The temperature of the suspension is also measured before and after, and the measurements are conducted at room temperature. The cells are suspended in media that is rich with nutrient, to keep them alive. Cells are subjected to light for less than 5 minutes (which is not significant time for the cells to die, mainly the cells during measurements suspended inside the media). Cell viability test is used to check the suspension before and after the optical measurements. Before the light percentage of living cell is above 90%, and after the optical measurements—the percentage of living cell is above 85%.

Figure 10A:
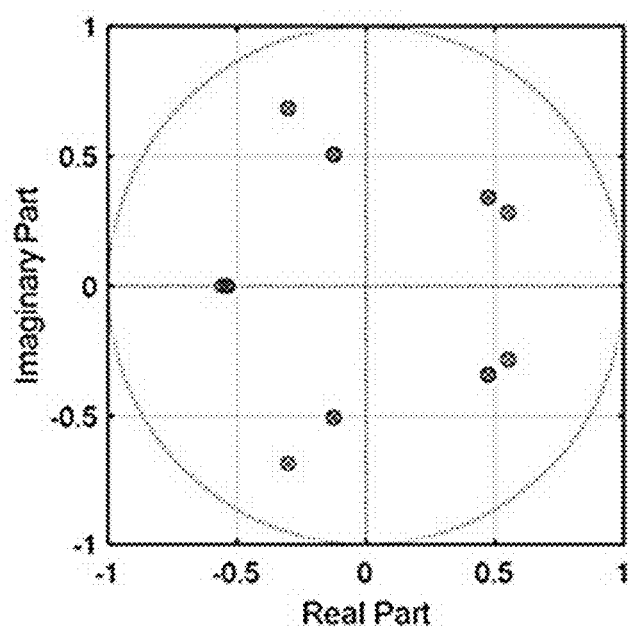
FIG. 10A shows the Z-plane showing distribution of the reduced poles of normal and cancerous lung cells and FIG. 10B shows the Z-plane showing distribution of normal and cancerous liver cells, in accordance with the present invention.
Figure 10B:
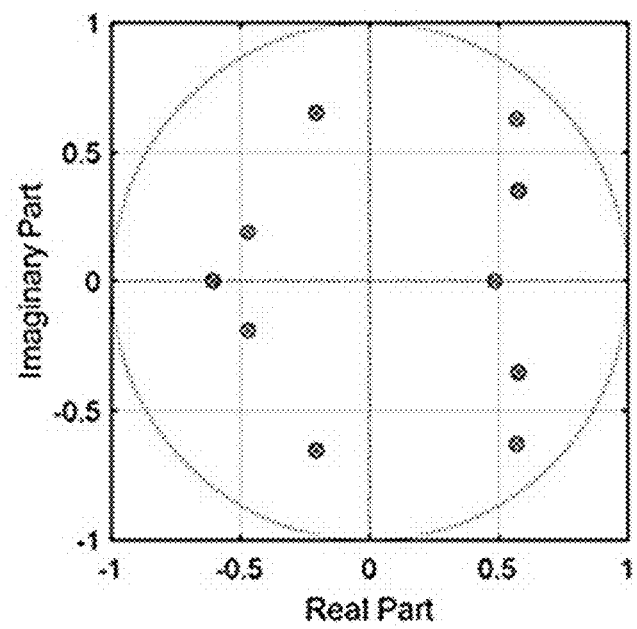

In an embodiment of the present invention, for reducing redundancy and to arrive at a concise AR model, statistical tools such as the N-way ANOVA technique are applied. The ANOVA revealed the significance of the AR coefficients. The ANOVA technique is applied to the AR coefficients rather than the poles since the poles were extracted from the coefficients. The coefficient that gives the highest value of the mean square is the significant AR coefficient. Three coefficients—a1, a3, and a5—out of the six coefficients shown in Table 4 are found to be significant. Hence the order of the AR model is reduced by one degree. This reduces the complexity of the system. A new set of reduced pole distribution in the Z-plan are plotted in FIG. 10. FIG. 10A shows the Z-plane showing distribution of the reduced poles of normal and cancerous lung cells and FIG. 10B shows the Z-plane showing distribution of normal and cancerous liver cells, in accordance with the present invention. The complex poles are defined as $\sigma \pm j\omega$, where $\sigma$ is the damping coefficient (real part of the pole) and $\omega$ is the resonant pulsation (imaginary part of the pole). The poles damping and resonant is used to identify the quality factor of the pole, as follows:

$$Q = \omega/2\sigma \quad (14)$$

In an embodiment of the present invention, the pole quality (Q) is then used to discriminate between cancer and normal cells. The pole quality is considered as a figure of merit (FOM), to correlate the real part with the imaginary part to develop a discrimination procedure. The location of the poles are strongly affected by differences in cell composition for normal and cancerous cells. Modifications of the optical response from normal to cancer state are explained mainly by morphological changes, modification of its physiological and biochemical properties that affect the refractive index and allowing them to be differentiated from each other; as previously indicated. The poles quality factors are affected accordingly. Empirically, the cancer cells exhibit higher transmittance intensity when compared to normal ones from the same tissue type.

Figure 11A:
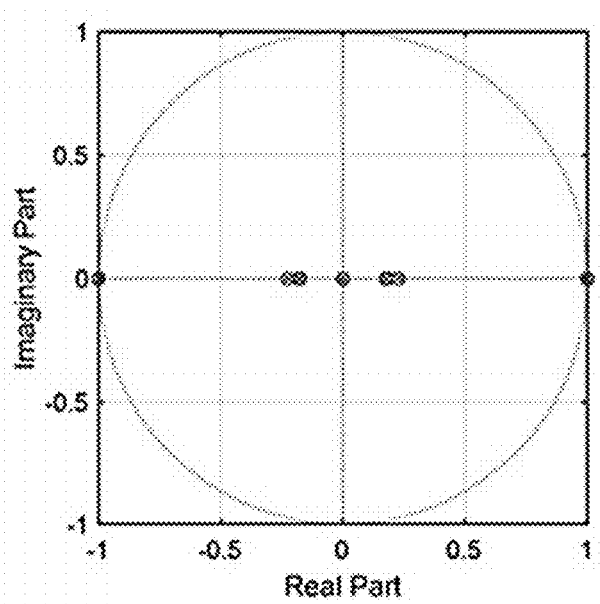
FIG. 11A depicts the Z-plane showing distribution of the Q-factor of normal and cancerous lung cells and FIG. 11B depicts the Z-plane showing distribution of the Q-factor of normal and cancerous liver cells, in accordance with the present invention.
Figure 11B:
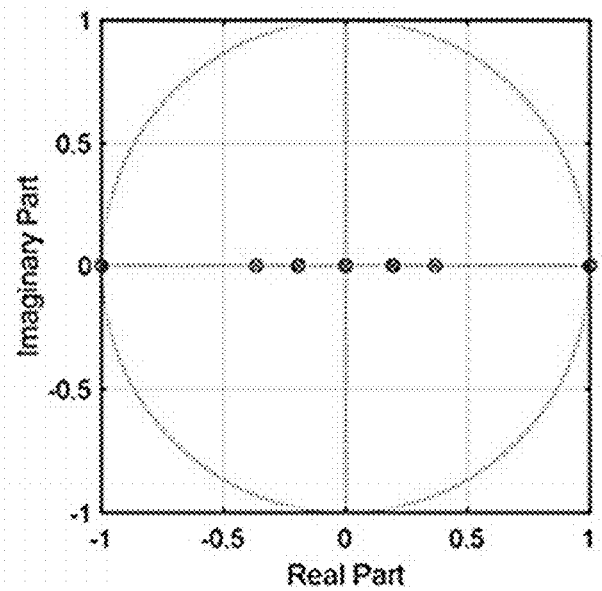

The corresponding computed poles quality factors for the four type of cells under study are shown in FIG. 11. FIG. 11A depicts the Z-plane showing distribution of the Q-factor of normal and cancerous lung cells and FIG. 11B depicts the Z-plane showing distribution of the Q-factor of normal and cancerous liver cells, in accordance with the present invention. FIG. 11 reveals that the magnitude of the pole quality factor for cancer cells is higher than normal. Therefore, the proposed approach offers a clear discrimination strategy—by performing optical measurements on the different in vitro cell normal and cancer cell line models, wherein the developed data processing procedure based on the AR method to achieve a label-free discrimination between cancer and healthy cells from the same tissue type works very well. Furthermore, the proposed approach may be coupled or integrated with existing techniques and methods to enhance the discrimination between cancer and normal cells from same tissues. The current method utilizes statistical methods that are less expensive than machine learning based methods.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A system for detection of cancerous cells from an organ tissue, the system comprising:
    a plurality of cells extracted from the organ tissue;
    a light source for directing light through the plurality of cells;

an image sensor configured to detect and measure optical transmission characteristics of the plurality of cells wherein the optical transmission characteristics comprise reflection, absorption and variable attenuation parameters, and a computer comprising software configured to model the optical transmission characteristics using a statistical algorithm, extract a plurality of data parameters from the modelled optical transmission characteristics, process the data parameters to obtain pole coefficients and locations corresponding to the plurality of cells, and calculate a figure of merit (FOM) for each of the plurality of cells to discriminate normal and cancerous cells, wherein the modeling comprises fitting the optical transmission characteristics with a sum of decaying exponential signals using Prony algorithm or using an Autoregressive (AR) modeling technique, and wherein the FOM is calculated from pole quality (Q) or the pole coefficients and locations corresponding to the plurality of cells.

2. The system of claim 1, wherein the plurality of cells extracted from the organ tissue are suspended in a cell culture medium.

3. The system of claim 1, wherein the image sensor detects and converts absorption, variable attenuation and reflectance, caused by the light source passing through the plurality of cells into electrical signals.

4. The system of claim 1, wherein variations in optical transmission characteristics of the plurality of cells are due to differences in cell composition and intrinsic characteristics between normal and cancerous cells.

5. The system of claim 1, wherein different coefficients and locations are due to differences in cell composition and intrinsic characteristics between normal and cancerous cells.

6. The system of claim 1, wherein the FOM is defined as $FOM(p)=C(p)/L(p)$, where $C(p)$ and $L(p)$ represent the pole coefficients and locations respectively, for the suspended plurality of cells.

7. The system of claim 1, wherein the software is configured to reconstruct the optical transmission characteristics using the Prony algorithm with a predefined fitting order.

\* \* \* \* \*